United States Patent [19]

Breads et al.

[11] Patent Number: 5,035,613
[45] Date of Patent: * Jul. 30, 1991

[54] ORTHODONTIC FINISHING POSITIONER AND METHOD OF CONSTRUCTION

[75] Inventors: Peter R. Breads, Grand Island; Gerard P. Abbatte, Buffalo; Stephen P. Warunek, West Seneca, all of N.Y.

[73] Assignee: Great Lakes Orthodontics, Ltd., Tonawanda, N.Y.

[*] Notice: The portion of the term of this patent subsequent to Aug. 15, 2006 has been disclaimed.

[21] Appl. No.: 75,327

[22] Filed: Jul. 20, 1987

Related U.S. Application Data

[63] Continuation-in-part of Ser. No. 46,087, May 5, 1987, Pat. No. 4,856,991.

[51] Int. Cl.⁵ ............................................. A61C 3/00
[52] U.S. Cl. ............................................. 433/6; 264/16; 128/861
[58] Field of Search ............... 433/6; 264/16; 128/861

[56] References Cited

U.S. PATENT DOCUMENTS

| | | | |
|---|---|---|---|
| 3,407,500 | 10/1968 | Kesling | 433/6 |
| 3,445,420 | 5/1969 | Kookootsedes et al. | 260/37 |
| 4,162,243 | 6/1979 | Lee et al. | 260/37 |
| 4,504,225 | 3/1985 | Yoshii | 433/6 |
| 4,551,096 | 11/1985 | Dellinger | 433/24 |
| 4,591,341 | 5/1986 | Andrews | 433/6 |
| 4,755,139 | 7/1988 | Abbatte et al. | 433/6 |

OTHER PUBLICATIONS

Silastic Eustachian Tube (Donaldson Design), Dow Corning Bulletin 51-043B dated Oct., 1983, Medical Materials, Dow Corning Corporation, Midland, Mich.
Silastic Tracheostomy Tube (Aberdeen Design), Dow Corning Bulletin 51-498 dated Jun., 1979, Medical Products, Dow Corning Corporation, Midland, Mich.
New Product Information, Silastic Q7-4840 A/B Medical Grade Liquid Silicone Rubber (LSR), Dow Corning Corporation, Midland, Mich., 1981.

*Primary Examiner*—Gene Mancene
*Assistant Examiner*—Adriene B. Lepiane
*Attorney, Agent, or Firm*—Hodgson, Russ, Andrews, Woods & Goodyear

[57] ABSTRACT

An orthodontic appliance for maloccluded teeth and an associated method of construction utilizes an elastomer base material comprised of a silicone elastomer composition. The elastomer composition, when in an uncured condition, possessses a sufficiently low viscosity so that the positioner can be formed in a low pressure injection molding process and which, when in a cured condition, possessses a relatively high resistance to tear.

14 Claims, 2 Drawing Sheets

Fig. 6.
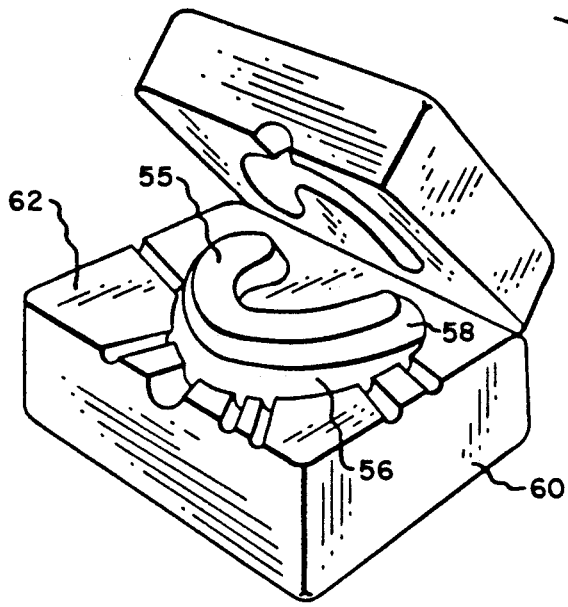
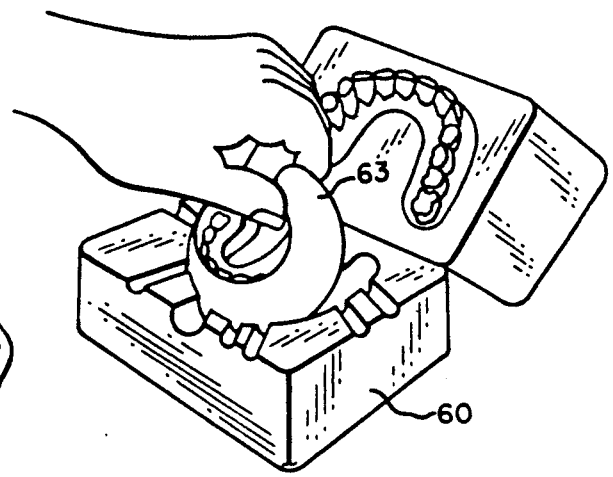
Fig. 8.
Fig. 9.
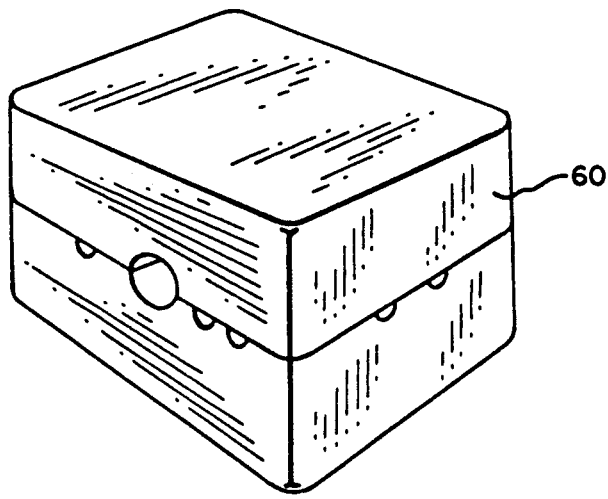
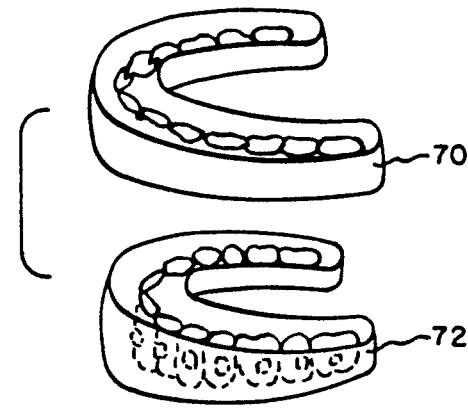
Fig. 7.

ORTHODONTIC FINISHING POSITIONER AND METHOD OF CONSTRUCTION

This application is a continuation-in-part of our pending application Ser. No. 046,087 filed May 5, 1987, issued Aug. 15, 1989, entitled ORTHODONTIC FINISHING POSITIONER AND METHOD OF CONSTRUCTION and having the same assignee as the present invention. The disclosure of referenced pending application Ser. No. 046,087 is incorporated herein by reference.

BACKGROUND OF THE INVENTION

This invention relates generally to the orthodontic treatment of maloccluded teeth and relates more particularly to a tooth positioner and an associated method of constructing the positioner.

In order to reposition a patient's teeth to a desired orientation, it is known that a positioner constructed of an elastomeric material and having an appearance resembling a common mouthguard can be operatively positioned about the patient's teeth for urging the teeth toward a predetermined or desired position. The positioner includes an arcuate-shaped body defining a trough or recess therealong for accepting the teeth when the positioner body is stretched therealong so that the stretched condition of the positioner body results in an urging of the teeth by the positioner toward a predetermined orientation.

It is an object of the present invention to provide a new and improved elastomeric positioner and an associated method of construction wherein the positioner has a relatively high resistance to damage by chewing or biting.

Another object is to provide such a positioner which is comprised of material facilitating a relatively rapid fabrication of the positioner.

Still another object of the present invention is to provide such a positioner comprised of material which is well-suited for use in low pressure injection molding process.

Yet still another object of the present invention is to provide such a positioner for exerting a force upon teeth which is within a range of acceptable orthodontic force levels.

A further object of the present invention is to provide such a positioner possessing desirable characteristics of durometer, flexibility, resiliency, elasticity and static compression.

A still further object of the present invention is to provide such a positioner possessing a clarity which does not detract from the appearance of the positioner.

SUMMARY OF THE INVENTION

This invention resides in an orthodontic positioner and an associated method of construction for realigning maloccluded teeth of a patient to a predetermined orientation.

The positioner of the present invention is comprised of a body constructed of an elastomer base material having an arcuate-shaped portion along which is defined a recess for receiving teeth of one dental arch of the patient. The improvement is characterized in that the elastomer base material is a silicone elastomer composition possessing a sufficiently low viscosity so that said positioner can be formed in a low pressure injection molding process and which, when cured, possesses a relatively high resistance to tear.

The method of the present invention includes the steps involved in constructing the positioner of this invention. Such steps include the providing of a construction model of the patient's teeth when the teeth therein are positioned in a predetermined orientation, providing an amount of uncured elastomer base material and forming the positioner out of the elastomer base material by applying the elastomer base material and permitting the elastomer base material to cure. The improvement is characterized in that the elastomer base material, when cured, possesses a relatively high tear resistance and elastic characteristics so that when the positioner is operatively stretched about the teeth in a deformed condition, the positioner urges the teeth toward the predetermined orientation and the force exerted by the positioner upon the teeth is within a range of orthodontically-acceptable force levels.

BRIEF DESCRIPTION OF THE DRAWING FIGURES

FIGS. 6 and 7 are perspective views of investment molding equipment utilized to form a positioner in accordance with an embodiment of the method of this invention.

FIG. 8 is a perspective view illustrating the removal of a molded positioner from the molding equipment of FIGS. 6 and 7.

FIG. 9 is a perspective view of yet still another embodiment of a positioner in accordance with the present invention.

DETAILED DESCRIPTION OF THE ILLUSTRATED EMBODIMENTS

Figure 1:
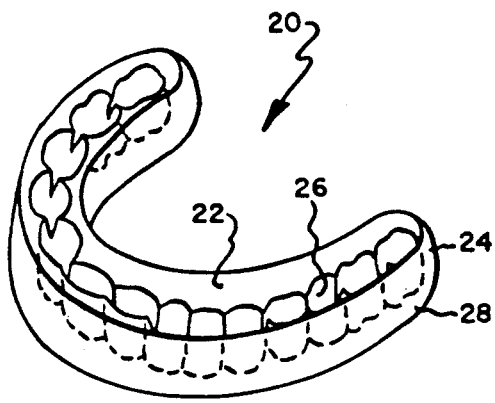
FIG. 1 is a perspective view of an embodiment of a positioner in accordance with the present invention.

Turning now to the drawings in greater detail and considering first FIG. 1, there is shown an orthodontic appliance, or positioner, generally indicated 20 and in accordance with the appliance of the present invention, for repositioning maloccluded teeth of the patient to a predetermined orientation. The positioner 20 is worn in a manner similar to the manner in which a common mouthguard is worn and possesses a resiliency which urges preselected ones of the patient's teeth to the predetermined orientation. As will be explained hereinafter, the positioner is constructed of material facilitating a relatively rapid formation of the positioner and provides the positioner 20 with desirable characteristics relating to its wear and wearability within the mouth and its capacity to urge the patient's teeth to the predetermined orientation.

The positioner 20 includes a unitary body 22 constructed of an elastomer base material 24, hereinafter described, having a teeth-accepting trough or recess 26 for closely and snugly accepting the teeth of one of the patient's dental arches. More specifically, the recess 26 of the positioner 20 is shaped in conformity to the general contours of the teeth of the upper dental arch of a patient when the teeth are oriented in a predetermined or desired orientation. Therefore, when the positioner 20 is operatively positioned about the maloccluded teeth, the body 22 is in a stretched or deformed condition thereabout and the elasticity or resiliency of the body 22 biases the teeth toward the predetermined orientation. Because the positioner 20 acts against teeth in only one dental arch of the patient, the positioner 20 is commonly referred to as a split positioner.

In accordance with the present invention, the elastomer base material 24 of the positioner body 22 is constructed of a material 28 which, when in an uncured condition, possesses a sufficiently low viscosity so that the positioner 20 can be formed in a low pressure injection molding process and which, when in a cured condition, possesses a relatively high resistance to tear. Because the material 28 can be injected-molded when in an uncured condition to form the desired positioner, it is believed that the positioner 20 can be formed much more quickly than can be a conventional positioner of elastomeric material requiring hand layup of the positioner in a piecemeal fashion. Furthermore, because the material, when in a cured condition, possesses a relatively high resistance to tear, the body 22 is less likely to be cut or otherwise damaged if chewed or bitten tightly when worn.

To this end, the material 28 out of which the positioner body 22 is constructed is a silicone rubber possessing a low viscosity when uncured and which, when cured, is a relatively tough, rubber elastomer. Materials found particularly well-suited for use as a material 28 are ones identified within a family of liquid silicone rubbers manufactured by Dow Corning Corporation, Midland, Mich. Such rubbers currently bear the Dow Corning trade designation SILASTIC and are identified as A/B Medical Grade Liquid Silicone Rubbers. One such liquid silicone rubber (LSR) is available under the designation SILASTIC Q7-4840 wherein the last two digits of the designation number indicate a Shore A durometer of the material of about 40. Two other LSDs in the family possess shore A durometers of about 50 and 65.

The following table sets forth test values obtained on an exemplary lot of SILASTIC Q7-4840 and set forth in the corresponding product literature published by Dow Corning Corporation.

|  | Value | CTM | ASTM |
|---|---|---|---|
| Specific Gravity | 1.12 | 0022 | D792 |
| Durometer Hardness, Share A, points | 40 | 0099 | D2240 |
| Tensile Strength, psi | 950 | 0137A | D412 |
| Elongation, percent | 425 | 0137A | D412 |
| Tear Strength, die B, ppi | 150 | 0159A | D624 |
| Tissue Culture | No CPE | 0274 | |
| Metals, ppm | | 0368 | |
| Al | 100 max | | |
| P | 50 max | | |
| Fe, Sb, Ge, Mg, Mn, Mo, Pb, Sn, Cr, Bi, Ti, Be, Ca, Ni, Ag, Co, Cu, Zr, Ba, As, Na, V | 10 ea., max | | |

Properties set forth in the foregoing table and listed under "value" were obtained on a 0.075 inch thick ASTM slab cured 5 minutes at 302° F. (150° C.) and allowed to equilibrate at room temperature for twenty-four hours. Furthermore, properties listed under CTM (Corporate Test Methods) correspond to standard ASTM tests in most instances.

Furthermore, the aforementioned SILASTIC LSR materials, when cured, possess a flexibility, elasticity and resiliency which provide a positioner 20 with strength or memory which urges the patient's teeth to a predetermined orientation with a force within a range of acceptable orthodontic or biological force levels. In other words, a positioner body 22 constructed of any of the aforementioned LSR materials are strong enough to effect a shifting of the patient's teeth when operatively worn thereabout over a period of time and not so strong that the teeth are damagably loosened by the body 22. Furthermore, a positioner 20 constructed of a SILASTIC LSR material possesses relatively slow force decay characteristics and desirable static compression characteristics in that the positioner 20 has a relatively good ability to bounce back to its original undeformed condition after being deformed. The referenced SILASTIC A/B LSRs are comprised of a two-part composition which parts are combined in appropriate portions prior to use. Cure of the composition mixture is initiated by the application of heat, and the rate of cure of the mixture can be controlled by controlling the amount of heat applied to the mixture. For example, the raising of the temperature of a mass of an LSR mixture comprised of SILASTIC Q7-4840 to about 230° F. (100° C.) cures the mass relatively rapidly.

Still further, the cured SILASTIC material possesses additional characteristics which are desirable in the positioner 20. For example, a positioner 20 comprised of a SILASTIC LSR possesses a desirable stretchability permitting the positioner body 22 to be easily stretched upon the teeth of a patient into an operative condition or removed from the patient's teeth. Additionally, a positioner 20 comprised of a SILASTIC LSR possesses sufficient clarity to render the positioner 20 esthetically appealing. This latter feature is advantageous when considering the fact that the positioner is to be worn within the mouth. Further still, the SILASTIC LSR materials are biocompatable rendering the positioner 20 biocompatable, as well.

In accordance with current product literature available from Dow Corning Corporation and relating to the SILASTIC material, the SILASTIC material is claimed in U.S. Pat. Nos. 3,445,420 and 4,162,243 whose disclosures are incorporated herein by reference. U.S. Pat. No. 4,162,243 describes a silicone elastic composition which is extrudable and which cures to a high strength, high durometer silicone elastomer. In view of the similarity of characteristics possessed by the positioner 20 comprised of a SILASTIC LSR and the advantages of the silicone elastic compositions set forth in U.S. Pat. No. 4,162,243, it is believed that of U.S. Pat. Nos. 3,445,420 and 4,162,243, the composition of the SILASTIC LSR is disclosed in at least U.S. Pat. No. 4,162,423.

In accordance with the disclosure of U.S. Pat. No. 4,162,234, a SILASTIC LSR is believed to be comprised of a mixture of a triorganosiloxy endblocked polydimethylsiloxane fluid, a reinforcing amphorous silica and a fluid organohydogensiloxane and a platinum catalyst.

U.S. Pat. No. 4,162,243 suggests, by way of example, that the triorganosiloxy endblock polydimethylsiloxane fluid is either dimethylvinylsiloxy or methylphenylvinylsiloxy and exists in the mixture in about 100 parts by weight. Furthermore, the reinforced silica has a surface area of greater than 100 meters per gram, and exists in the mixture in about 20 to 60 parts by weight. The fluid organohydrogensiloxane consists essentially of units selected from a group consisting of methylhydrogeusiloxane, dimethylsiloxane, dimethylhydrogensiloxy, trimethylsiloxy and $SiO_2$ units. A platinum catalyst inhibitor can be optionally added to the mixture to increase its shelf life. For a more detailed description of the silicone elastomer composition described in U.S. Pat. No. 4,162,243, reference may be had to U.S. Pat. No. 4,162,243.

Figure 2:
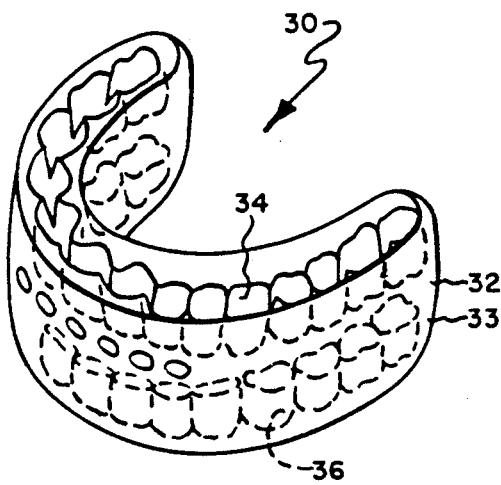
FIG. 2 is a perspective view of another embodiment of a positioner in accordance with the present invention.

With reference to FIG. 2, there is illustrated an alternative embodiment generally indicated 30, of a positioner in accordance with the appliance of the present invention. The positioner 30 includes a unitary body 32 constructed of an elastomer based material 33 having a pair of teeth-accepting recesses or troughs 34, 36 for closely and snugly accepting the teeth of the upper and lower dental arches of a patient. The recesses 34, 36 are shaped in conformity to the general contours of the teeth of the patient when the teeth are oriented in a predetermined or desired orientation. Therefore, the body 32 is positionable within the patient's mouth so that the body 32 is operatively stretched about the teeth in both the upper and lower dental arches, the positioner body 32 effectively biases maloccluded teeth in each of the upper and lower dental arches toward a predetermined orientation as the body 32 attempts to return to its relaxed or undeformed condition. Because the positioner 30 acts against teeth in both the upper and lower dental arches of the patient, the positioner 30 is commonly referred to as a full positioner.

In accordance with the present invention, the elastomer base material 33 out of which the positioner body 32 is constructed possesses characteristics permitting its use, when in an uncured condition, in an injection molding process to form the positioner 30 and which, when cured, provides the positioner 30 with high resistance to tear. By way of example, the material 33 can be constructed out of a material equivalent to the SILASTIC LSR material discussed above and which possesses the aforedescribed characteristics associated with the SILASTIC LSR material.

Figure 3:
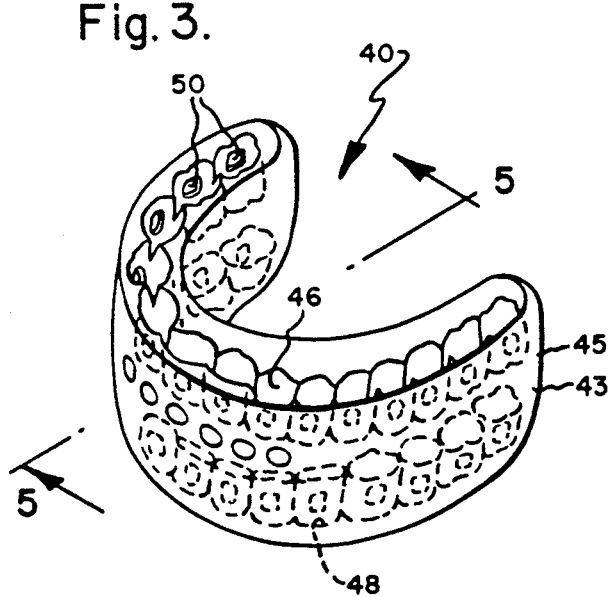
FIG. 3 is a perspective view of still another embodiment of a positioner in accordance with the present invention.
Figure 4:
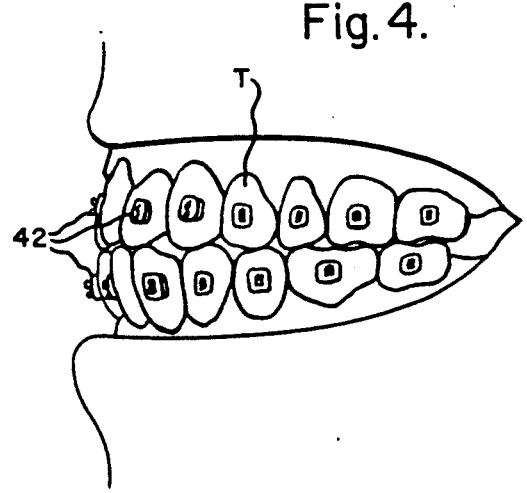
FIG. 4 is a perspective view of a patient's teeth about which the FIG. 3 positioner has been designed to be operatively positioned.
Figure 5:
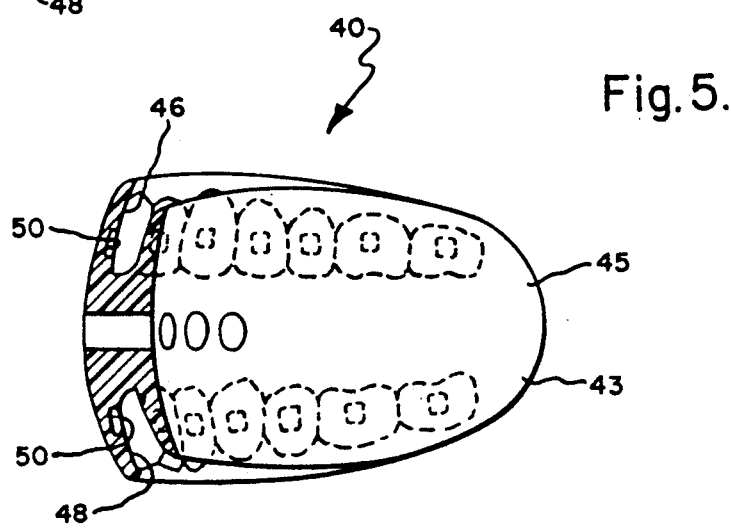
FIG. 5 is a cross-sectional view taken about on lines 5—5 of FIG. 3.

With reference to FIGS. 3 and 5, there is shown an orthodontic positioner, generally indicated 40, in accordance with the appliance of the present invention for repositioning maloccluded teeth T (FIG. 4) of a patient P to a predetermined orientation and to which coupling members 42 are attached. Although the coupling members 42 can take any a number of forms in the interests of this invention, the coupling members 42 are in the form of retaining brackets of the type commonly used in connection with arch wires (not shown) of orthodontic braces.

The positioner 40 includes a unitary body 45 constructed of an elastomer base material 43 having a pair of teeth-accepting recesses 46, 48 for closely and snugly accepting the teeth T to which coupling members 42 are secured. The recesses 46, 48 are shaped in conformity to the general contours of the teeth T and the coupling members 42 when the teeth T are oriented in a predetermined or desired orientation. Furthermore and as best shown in FIG. 5, each recess 46 or 48 includes walls defining a series of indentations 50 shaped to nestingly accept a corresponding coupling member 42 of the corresponding upper or lower dental arch of the patient when the positioner body 45 is operatively positioned thereabout.

An advantage provided by the positioner 40 relates to its ability to grasp the maloccluded teeth T for the purpose of transferring elastic force potential from the positioner body 45 to the teeth T. To this end and when the positioner 40 is positioned about the teeth T, the indentations 50 of the recesses 46 and 48 are stretched about so as to nestingly accept the coupling members 42 and the remainder of the recess walls are stretched about so as to nestingly accept the crowns of the teeth T. It follows that the coupling members 42 and indentations 50 coact as male and female couplers, respectively to enhance the securement of the body 45 to the teeth T, and cooperate to provide an effective grasping of the coupling members 42 by the body 45. Such an effective grasping of the brackets 42 is believed to enhance the transfer of elastic force potential from the positioner to the teeth T and to thereby efficiently utilize the elasticity of the positioner body 40.

In accordance with the appliance of the present invention, the elastomer base material 43 out of which the positioner 40 is constructed is SILASTIC LSR or an equivalent material so that the positioner 40 can be formed in an injection molding process and is provided with a high resistance to tear.

With reference to FIGS. 6–8, the method of the present invention includes the steps involved in constructing a positioner in accordance with the present invention. In order to construct a split positioner, such as positioner 20 of FIG. 1, a construction model of the teeth in one of the upper or lower dental arches is provided when the teeth therein are positioned in a predetermined orientation. Briefly, a construction model 56 can be made by forming an impression of the preselected dental arch, utilizing the impression to form a die stone facsimile, cutting the teeth-simulating portions of the facsimile from the remainder of the facsimile and forming a wax/stone combination model wherein the teeth-simulating portions are reset in the orientation in which the patient's teeth are desired to be positioned. A duplication of the wax/stone model is formed with die stone to provide the construction model. For more detail of the steps involved in constructing a construction model, reference may be had to our pending application Ser. No. 046,087 filed May 5, 1987.

A wax pattern 55 of the desired positioner is then built upon the construction model 56 so as to provide a pattern-supporting construction model 58, and investment molding equipment, such as an injection-type flask 60, is provided for forming the desired positioner with injection molding techniques. Briefly, the pattern-supporting construction model 58 is operatively placed within the flask 60 and a plaster investment 62 is poured around the model 56 and pattern 55 placed therein. The wax pattern 55 is boiled out to define a mold cavity, and replaced with an amount of uncured elastomer base material 63 injected into the mold cavity. Heat is thereafter applied to the flask 60 to cure the material 63, and the formed positioner is thereafter removed from the flask 60. The positioner can then be finished, as by trimming with scissors, to remove material flash from vents and the sprue of the mold.

In accordance with the method of the present invention, the uncured elastomer base material 63 possesses a sufficiently low viscosity so that the material 63 can be introduced into the flask 60 with relatively low injection pressures. Furthermore the material 63 is characterized in that, when cured, it possesses a relatively high tear resistance. By way of example, a material comprising the material 63 is a SILASTIC LSR or an equivalent material.

If a SILASTIC LSR material is used as the elastomer base material 63, it is recommended by Dow Corning Corporation that airless mixing, metering and dispensing equipment is recommended for production operations. Furthermore, work areas must be relatively clean so that foreign materials cannot poison the catalyst thereby inhibiting the cure.

In order to form a full positioner of the type illustrated in either FIG. 2 or FIGS. 3 and 5, construction models must be provided of both the upper and lower dental arches of the patient and the wax pattern of the desired positioner must be built upon both construction models. Both construction models, bearing the pattern of the full positioner, are then placed within the flask 60, and the wax replaced with elastomer base material in an injection molding process. As is the case with the formation of the split positioner described above, the elastomer base material out of which the full positioner is formed is a SILASTIC LSR or an equivalent material.

It will be understood that numerous modifications and substitutions can be had to the aforedescribed embodiments without departing from the spirit of the invention. For example, although the positioner 40 of FIGS. 3 and 5 described above for use in cooperation with teeth-mounted coupling members has been shown and described above as a full positioner, a positioner for coaction with teeth-mounted coupling members may be a split positioner. For example, there is illustrated in FIG. 9 a pair of split positioners 70,72 adapted to be operatively positioned about the teeth in the upper and lower, respectively, dental arches of a patient wherein the teeth of each arch supportedly carries coupling members. In accordance with the present invention, the material out of which the split positioners 70 and 72 are comprised is a SILASTIC LSR or an equivalent material. Accordingly, the aforedescribed embodiments are intended as illustration and not as limitation.

We claim:

1. An orthodontic appliance for maloccluded teeth including a monolithic body of elastomer base material having an arcuate-shaped portion along which is defined a recess for receiving teeth of one dental arch of the patient wherein the teeth include maloccluded teeth to which are secured coupling members, the recess having walls defining teeth-engaging surfaces shaped generally complementary to the surfaces of the teeth of said one arch when the maloccluded teeth thereof are positioned in a predetermined orientation and defining a series of indentations formed in the material of said body and disposed across said teeth-engaging surfaces, each indentation shaped in the material of said body to nestingly accept a corresponding protruding coupling member portion when placed thereabout so that when said appliance body is operatively positioned within the patient's mouth and stretched about the teeth of the one dental arch so that the teeth thereof are accepted by the recess of said arcuate-shaped portion and each protruding coupling member portion is nestingly accepted by a corresponding indentation, the stretched body acts directly against the teeth and the coupling member portion to urge the teeth toward a desired orientation, the improvement characterized in that:

the elastomer base material is a silicone elastomer composition which, when in an uncured condition, is liquid and possesses a sufficiently low viscosity so that said positioner can be formed in a low pressure injection molding process, which composition is curable to a solid form by the application of heat so that the rate of cure can be controlled by controlling the amount of heat applied, and which, when in a cured condition, possesses a relatively high resistance to tear and an inherent strength for urging preselected ones of the teeth toward a predetermined orientation wherein the positioner forces for acting upon the teeth are within a range of orthodontically-acceptable force levels.

2. The improvement of claim 1 wherein the silicone elastomer composition, when cured, is relatively clear.

3. The improvement of claim 1 wherein the silicone elastomer composition, when cured, resists absorption of water.

4. The improvement of claim 1 wherein the silicone elastomer composition is a medical grade liquid silicone rubber.

5. An orthodontic appliance for maloccluded teeth to which are operatively secured coupling members and wherein the appliance includes a monolithic body constructed of an elastomer base material having an arcuate portion along which is shaped a recess for receiving teeth of one dental arch of the patient, the recess having walls defining teeth-engaging surfaces shaped generally complementary to the surfaces of the teeth of said one arch when the maloccluded teeth thereof are positioned in a predetermined orientation and defining a series of indentations formed in the material of said body and disposed across said teeth-engaging surfaces, each indentation shaped in the material of said body to nestingly accept a corresponding protruding coupling member portion when placed thereabout so that when said appliance body is operatively positioned within the patient's mouth and stretched about the teeth of the one dental arch so that the teeth thereof are accepted by the recess of said arcuate-shaped portion and each protruding coupling member portion is nestingly accepted by a corresponding indentation, the stretched body acts directly against the teeth and the coupling members to effectively bias the teeth of said one arch toward the predetermined orientation, the improvement characterized in that:

the elastomer base material is formed from a silicone elastomer composition in the form of a medical grade liquid silicone rubber possessing, when in an uncured condition, viscous characteristics permitting the material to be injection molded at low pressures and which, when cured, possesses a relatively high tear resistance, said silicone elastomer composition including two parts which when mixed in appropriate portions, is curable to a tough, rubbery elastomer via addition-cure chemistry, said silicone elastomer composition possessing, when cured, an inherent strength for urging preselected ones of the teeth toward a predetermined orientation wherein the positioner forces for acting upon the teeth are within orthodontically-acceptable force levels.

6. A method of constructing an orthodontic positioner for maloccluded teeth located in a preselected one of the upper and lower dental arches of a patient wherein the maloccluded teeth of the patient supportedly carry coupling members of the type including portions protruding from the teeth, the method including the steps of providing a construction model of the patient's teeth in the preselected dental arch when the teeth therein are positioned in a predetermined orientation, providing an amount of uncured elastomer base material and forming the positioner out of said elastomer base material by low pressure injection molding including applying said elastomer base material about said construction model and permitting said elastomer base material to cure, the construction model including either portions simulating the coupling members or coupling members attached to the teeth-simulating portions of the construction model so that the applying of elastomer base material about the construction model shapes the elastomer material about the coupling member-simulating portions of the coupling members so that the subsequently-formed positioner is a monolithic body adapted to coact with the teeth and coupling members to effectively bias the teeth of the preselected arch toward the predetermined orientation, the improvement characterized in that the elastomer base material, when uncured, is a medical grade liquid silicone rubber which possesses a sufficiently low viscosity so that said positioner can be formed in a low pressure injection molding process and which, when cured, possesses a relatively high tear resistance and possesses elastic characteristics so that when the positioner is operatively stretched about the teeth in a deformed condition, the positioner urges the teeth toward the predetermined orientation and the force exerted by the positioner upon the teeth is within a range of orthodontically-acceptable force levels.

7. The improvement of claim 6 wherein said step of forming the positioner includes the steps of:

building a wax pattern of the desired positioner upon said construction model so as to provide a pattern-supporting construction model, which positioner includes a part adapted to be positioned about at least the teeth, protruding portions of the coupling members and gum tissue portion of the preselected dental arch;

providing investment molding equipment with which the positioner is to be constructed;

operatively positioning the pattern-supporting construction model within the investment molding equipment and utilizing investment molding techniques to replace the wax pattern within the molding equipment with the uncured amount of elastomer base material;

permitting the amount of elastomer base material to cure to thereby provide the positioner;

removing the positioner from the investment molding equipment.

8. The improvement of claim 6 wherein the elastomer base material, when cured, resists the absorption of water.

9. The improvement of claim 6 wherein the elastomer base material, when cured, is relatively clear.

10. An orthodontic appliance for maloccluded teeth including a body of elastomer base material having an arcuate-shaped portion along which is defined a recess for receiving teeth of one dental arch of the patient and urging preselected ones of the teeth toward a desired orientation, the improvement characterized in that:

the elastomer base material is a silicone elastomer composition which, when in an uncured condition, possesses a sufficiently low viscosity so that said positioner can be formed in a low pressure injection molding process and which, when in a cured condition, possesses a relatively high resistance to tear, said silicone elastomeric composition including a mixture of triorganosiloxy endblocked polydimethylsiloxane fluid, a reinforcing amorphous silica and a fluid organohydrogensiloxane and a platinum catalyst.

11. The improvement of claim 10 wherein said triorganosiloxy endblocked polydimethylsiloxane fluid is present in said composition in about 100 parts by weight and said reinforcing amorphous silica is present in said composition in about 20 to 60 parts by weight.

12. An orthodontic appliance for maloccluded teeth including a body of elastomer base material having an arcuate-shaped portion along which is defined a recess for receiving teeth of one dental arch of the patient and urging preselected ones of the teeth toward a desired orientation, the improvement characterized in that:

the elastomer base material is a silicone elastomer composition which, when in an uncured condition, possesses a sufficiently low viscosity so that said positioner can be formed in a low pressure injection molding process and which, when in a cured condition, possesses a relatively high resistance to tear, said silicone elastomer composition including a platinum catalyst.

13. An orthodontic appliance for maloccluded teeth to which are operatively secured coupling members and wherein the appliance includes a body constructed of an elastomer base material having an arcuate portion along which is shaped a recess for receiving teeth of one dental arch of the patient wherein said body cooperates with said coupling members and teeth so that when operatively positioned thereabout, the stretched body acts against the teeth and coupling members to effectively bias the teeth of said one arch toward the predetermined orientation, the improvement characterized in that:

the elastomer base material is formed from a silicone elastomer composition possessing, when in an uncured condition, viscous characteristics permitting the material to be injection molded at low pressures and which, when cured, possesses a relatively high tear resistance, said silicone elastomeric composition including a mixture of triorganosiloxy endblocked polydimethylsiloxane fluid, a reinforcing amorphous silica and a fluid organohydrogensiloxane and a platinum catalyst.

14. A method of constructing an orthodontic positioner for maloccluded teeth located in a preselected one of the upper and lower dental arches of a patient including the steps of providing a construction model of the patient's teeth in the preselected dental arch when the teeth therein are positioned in a predetermined orientation, providing an amount of uncured elastomer base material and forming the positioner out of said elastomer base material by injection molding including applying said elastomer base material about said construction model and permitting said elastomer base material to cure, the improvement characterized in that:

the elastomer base material, when uncured, possesses a sufficiently low viscosity so that said positioner can be formed in a low pressure injection molding process and which, when cured, possesses a relatively high tear resistance and possesses elastic characteristics so that when the positioner is operatively stretched about the teeth in a deformed condition, the positioner urges the teeth toward the predetermined orientation and the force exerted by the positioner upon the teeth is within a range of orthodontically-acceptable force levels, said elastomer base material including a mixture of triorganosiloxy endblocked polydimethylsiloxane fluid, a reinforcing amorphous silica and a fluid organohydrogensiloxane and a platinum catalyst.

* * * * *